(12) United States Patent
Gatzemeyer et al.

(10) Patent No.: US 8,075,216 B2
(45) Date of Patent: Dec. 13, 2011

(54) ORAL CARE IMPLEMENT HOUSING AN ORAL CARE AGENT

(75) Inventors: John J. Gatzemeyer, Hillsborough, NJ (US); Bruce M. Russell, Howell, NJ (US); Kenneth Waguespack, North Brunswick, NJ (US); Thomas J. Boyd, Metuchen, NJ (US)

(73) Assignee: Colgate-Palmolive Company, New York, NY (US)

( * ) Notice: Subject to any disclaimer, the term of this patent is extended or adjusted under 35 U.S.C. 154(b) by 1238 days.

(21) Appl. No.: 11/626,855

(22) Filed: Jan. 25, 2007

(65) Prior Publication Data

US 2008/0181716 A1  Jul. 31, 2008

(51) Int. Cl.
*A47L 13/22* (2006.01)

(52) U.S. Cl. ............ 401/288; 401/23; 401/24; 401/270; 401/282; 401/283

(58) Field of Classification Search .......... 401/183–186, 401/270, 274, 278, 282, 283, 284, 288, 23, 401/24

See application file for complete search history.

(56) References Cited

U.S. PATENT DOCUMENTS

| | | | |
|---|---|---|---|
| 1,963,389 A | 6/1934 | Vardeman | |
| 2,099,688 A | 11/1937 | Hill et al. | |
| 2,216,333 A | 10/1940 | White et al. | |
| 3,302,230 A | 2/1967 | Poppelman | |
| 3,353,898 A * | 11/1967 | Lamberti | 401/132 |
| 3,853,412 A * | 12/1974 | Griffin | 401/183 |
| 3,995,648 A * | 12/1976 | Kuryla | 401/173 |
| 4,039,261 A | 8/1977 | Evans | |
| 5,061,106 A | 10/1991 | Kent | |
| 5,366,310 A * | 11/1994 | Armelles Flors | 401/132 |
| 5,476,384 A | 12/1995 | Giuliani et al. | |
| 5,609,431 A * | 3/1997 | Carroll | 401/201 |
| 5,836,769 A | 11/1998 | Spencer | |
| 5,865,195 A | 2/1999 | Carter | |
| 5,908,038 A | 6/1999 | Bennett | |
| 5,915,868 A * | 6/1999 | Frazell | 401/132 |
| 6,108,850 A | 8/2000 | McLaughlin | |
| 6,260,229 B1 | 7/2001 | Edwards et al. | |
| 6,408,473 B1 | 6/2002 | Kessler | |
| 6,434,778 B1 | 8/2002 | Edwards et al. | |
| 6,453,497 B1 | 9/2002 | Chiang et al. | |
| 6,602,013 B2 * | 8/2003 | Clark | 401/282 |
| 6,871,374 B2 | 3/2005 | Brezler, III et al. | |
| 7,273,327 B2 * | 9/2007 | Hohlbein et al. | 401/132 |
| 7,674,058 B2 * | 3/2010 | Berger et al. | 401/7 |

(Continued)

FOREIGN PATENT DOCUMENTS

BE  894029 A2  1/1982

(Continued)

OTHER PUBLICATIONS

International Search Report Dated Jul. 2, 2008.

(Continued)

*Primary Examiner* — David Walczak
(74) *Attorney, Agent, or Firm* — Judy W. Chung (57) ABSTRACT

An oral care implement may include a tufted insert and a base configured to define a cavity for housing an active insert. The active insert may comprise an active agent. The head of the oral care implement may be configured so that the active insert can be in fluid communication with a membrane or an aperture.

31 Claims, 9 Drawing Sheets

U.S. PATENT DOCUMENTS

| | | |
|---|---|---|
| 2001/0038914 A1 | 11/2001 | Guay et al. |
| 2003/0115702 A1 | 6/2003 | Edwards |
| 2006/0101597 A1 | 5/2006 | Donnelly |
| 2008/0014010 A1 | 1/2008 | Bartschi et al. |

FOREIGN PATENT DOCUMENTS

| | | |
|---|---|---|
| FR | 2646068 A | 10/1990 |
| RU | 2116042 | 7/1998 |
| TW | 120555 | 10/1989 |
| WO | 8801839 A | 3/1988 |
| WO | 0053053 A | 9/2000 |
| WO | WO2006/032367 A1 | 3/2006 |

OTHER PUBLICATIONS

Decision on Grant from the Patent Office of the Russian Federation dated Oct. 25, 2010 for corresponding Russian Patent Application No. 2009131932.

* cited by examiner

ORAL CARE IMPLEMENT HOUSING AN ORAL CARE AGENT

FIELD OF THE INVENTION

The present invention relates to an oral care implement having an agent that can be delivered within the mouth of a user to provide enhanced oral heath.

BACKGROUND OF THE INVENTION

People exhibit many forms of poor oral health including tooth decay, periodontal diseases and bad breath (halitosis). Tooth decay and periodontal disease are typically caused by harmful bacteria within the mouth. When the harmful bacteria mixes with proteins present in saliva, a film of plaque is formed on the teeth and soft tissue. If the plaque is not removed, it can attack the teeth and create cavities. Additionally, the plaque will attack the soft tissue within the mouth and cause gum disease, the leading cause of tooth loss in adults. As a result, decreasing the amount of harmful bacteria in the mouth has long been the target of persons working in the oral health care field.

The most common way of minimizing the harmful bacteria within the mouth is brushing with a dentifrice that delivers at least one oral care agent into the mouth. Orally introduced liquids, including oral rinses, are also utilized to provide additional oral care beyond that achieved while brushing. Mouthwashes may also be used to deliver breath freshening agents within the mouth in an attempt to eliminate bad breath.

Unfortunately, individuals do not always have the time for adequate oral care. For example, a busy person may not have the time or patience to brush thoroughly, floss and/or use an oral rinse. Alternatively, certain people may consider anything more than brushing their teeth to be unnecessary. For either reason, these people may leave a significant amount of harmful bacteria within their mouths after completing their oral care routines, which can begin to attack the teeth and gums.

Hence, there is a need for a toothbrush that delivers an agent during brushing to improve oral health.

BRIEF SUMMARY OF THE INVENTION

The present invention pertains to an oral care implement having an agent that can be delivered within the mouth of a user to provide enhanced oral health.

An aspect of the present invention pertains to an oral care implement that delivers an oral care agent to the mouth of a user via an aperture or porous membrane.

In one aspect, the oral care implement includes a head having at least a portion formed so as to define one or more cavities. At least one oral care agent is provided in one or more of the cavities and dispensed within the mouth of a user when the oral care agent contacts a fluid or chemical within the oral cavity.

In one aspect, an oral care implement includes an oral care active agent located within one or more cavities of the head. The agent may be dispensed through a tuft head plate.

In one aspect, an oral care implement includes an oral care active agent located within one or more cavities of the head. The agent may be dispensed through a membrane disposed opposite of a tuft head plate.

In one aspect, an oral care implement includes an oral care active agent located within one or more cavities of the head. The agent may be dispensed through tufted head plate having at least one aperture and a membrane disposed opposite of a tufted head plate.

In one aspect, the oral care implement can be reusable or disposable. The oral care active agents can be released during a single use, during multiple uses, or throughout the useable life of the implement. Water, oral secretions and/or chemicals within the mouth can activate the oral care agents.

DETAILED DESCRIPTION OF THE INVENTION

Figure 1:
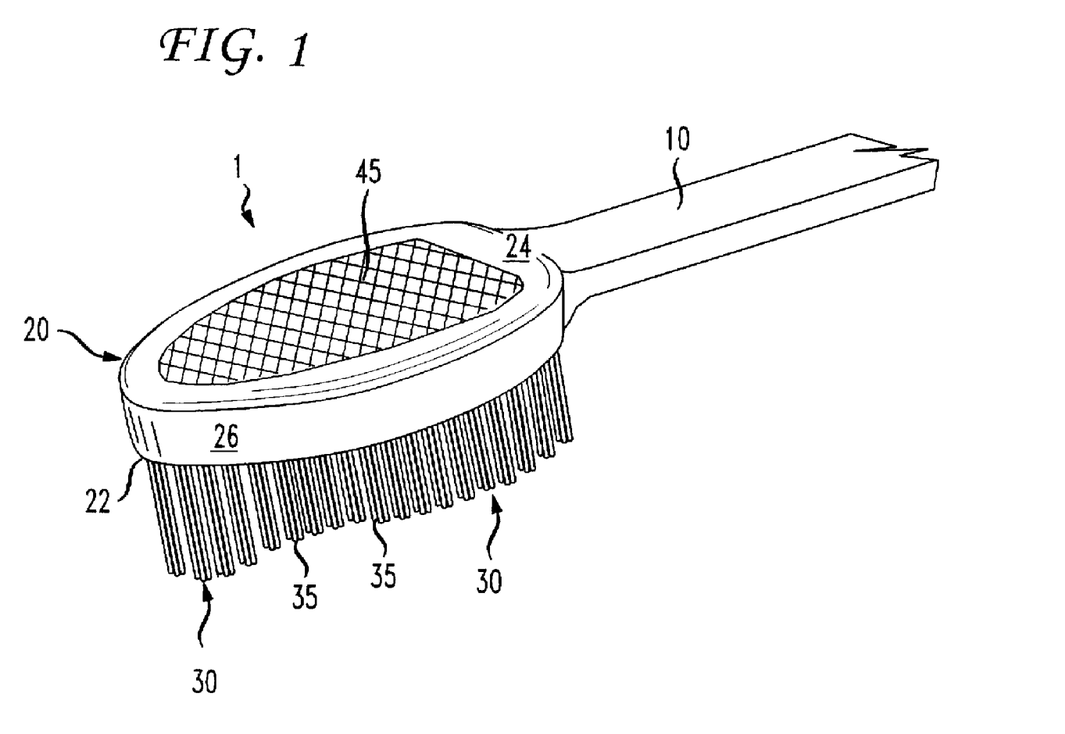
FIG. 1 is a perspective view of an oral care implement construction.

FIG. 1 illustrates an oral care implement 1 having an elongated handle 10 and a head 20 intended to be introduced into the mouth or oral cavity of a user. The oral care implement 1 is not limited to a toothbrush as shown and described, but can have any shape or structure and perform any function that permits it to deliver oral care agents to the user, with non-limiting examples of other oral care implements including tongue cleaners and portable brush, toothpick combinations. In one arrangement, the oral care implement can be used once and then discarded, or it can be used repeatedly over a period of time. The elongated handle 10 may be formed of a variety of shapes and with a variety of constructions that permit the oral care implement 1 to be readily gripped and manipulated within the mouth of the user.

Figure 2:
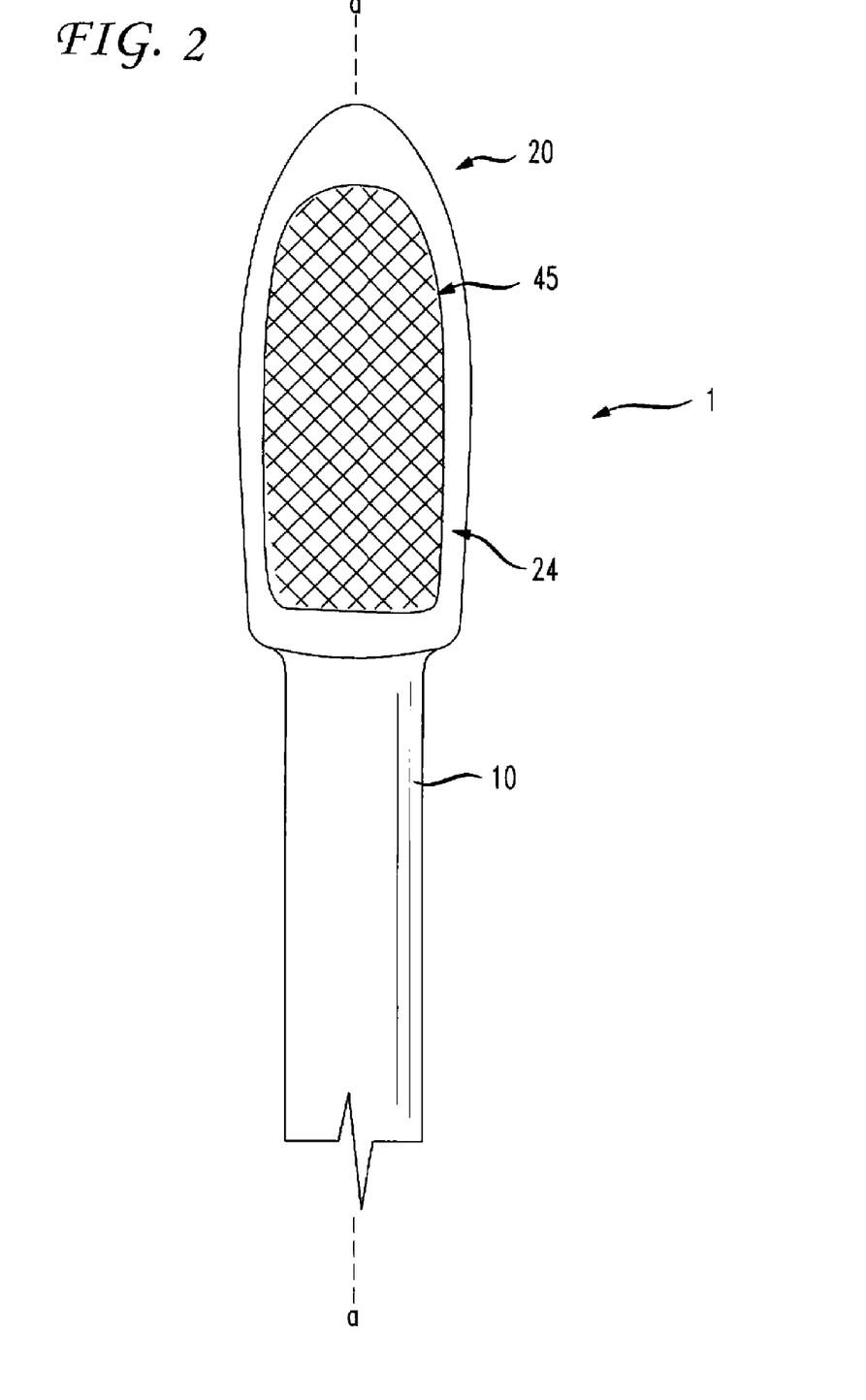
FIG. 2 is a view of one surface of the oral care implement of FIG. 1.
Figure 3:
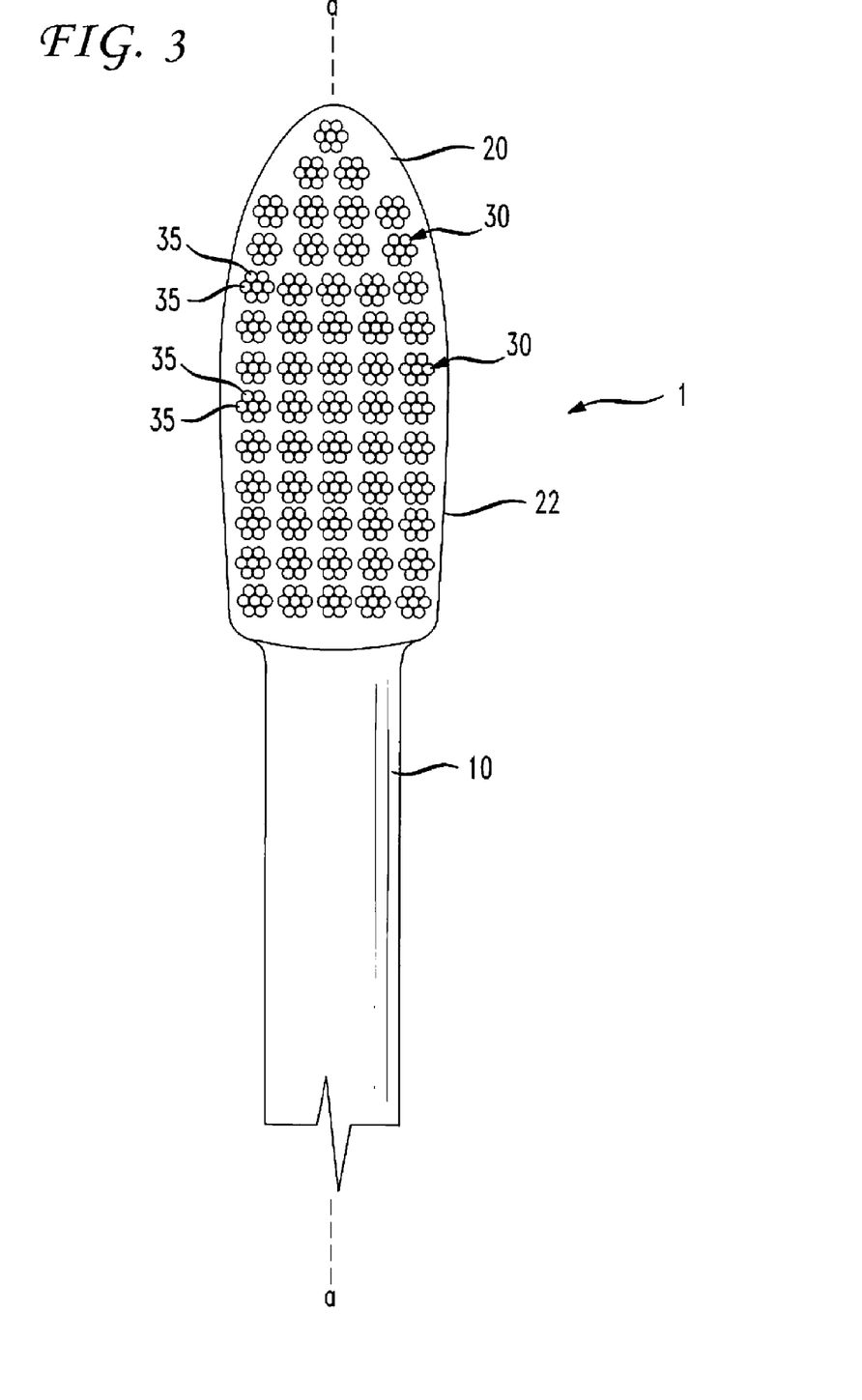
FIG. 3 illustrates a surface of the oral care implement of FIG. 1 taken opposite FIG. 2.

The head 20 includes multiple surfaces that are exposed to fluids within the mouth during use. In the embodiment illustrated in FIGS. 1-3, the head 20 includes a first surface 22 and an opposing second surface 24. Sidewalls 26 extend between the surfaces 22, 24. Oral care elements 30 can extend from either or both surfaces 22, 24 of the head 20, which elements 30 can include tooth cleaning elements 35, such as elongated bristles or elastomeric fingers, or soft tissue cleaning elements such as tongue cleaning members (not shown) extending from either surface 22, 24.

The oral care elements 30 disclosed herein are not limited to those discussed above. The oral care elements include "tooth cleaning elements" or "cleaning elements" which can be any type of structure that is commonly used or is suitable for use in providing oral health benefits (e.g., tooth cleaning, tooth whitening, tooth polishing, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members.

Figure 4A:
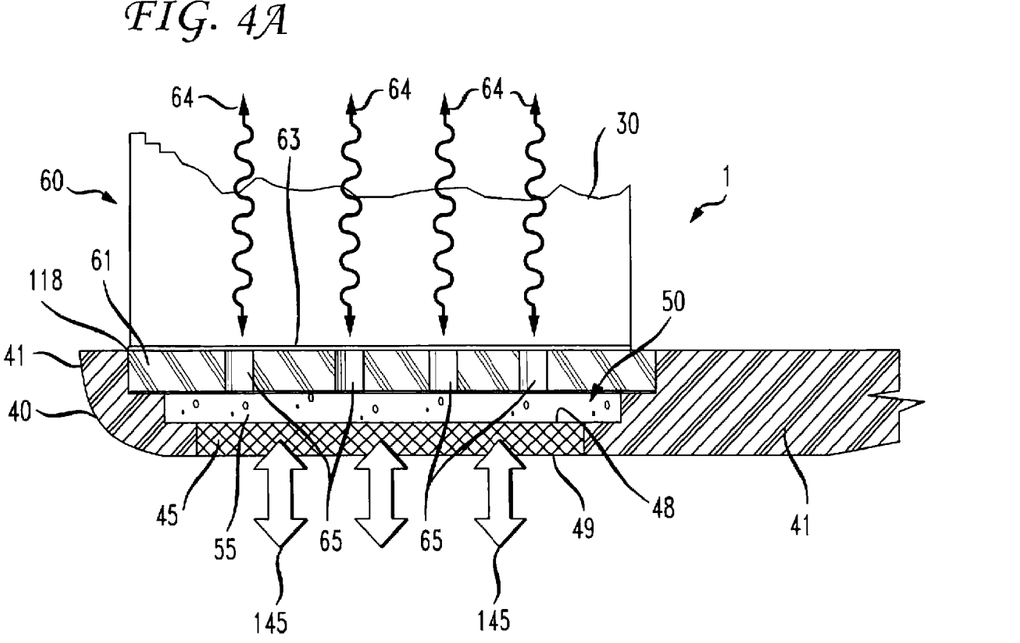
FIG. 4A is a side view of the oral care implement of FIG. 1.
Figure 4B:
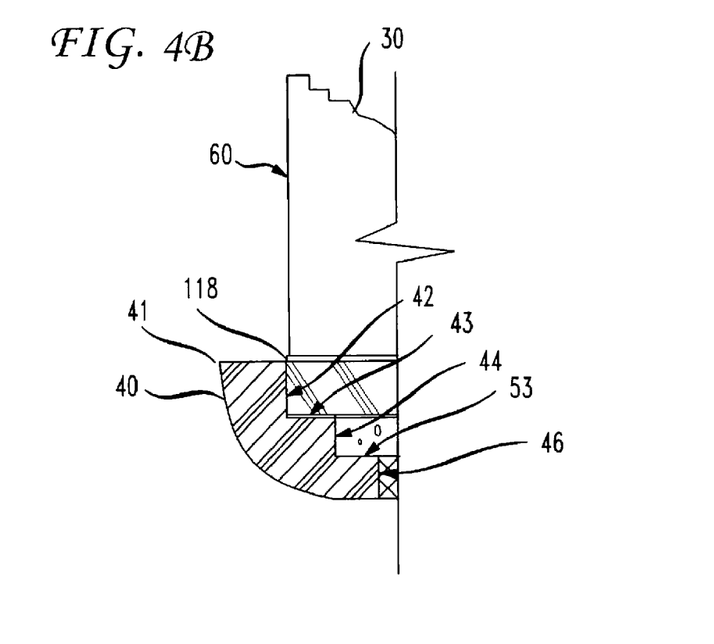
FIG. 4B is an enlarged fragmentary view of the head of the oral care implement of FIG. 1.
Figure 5:
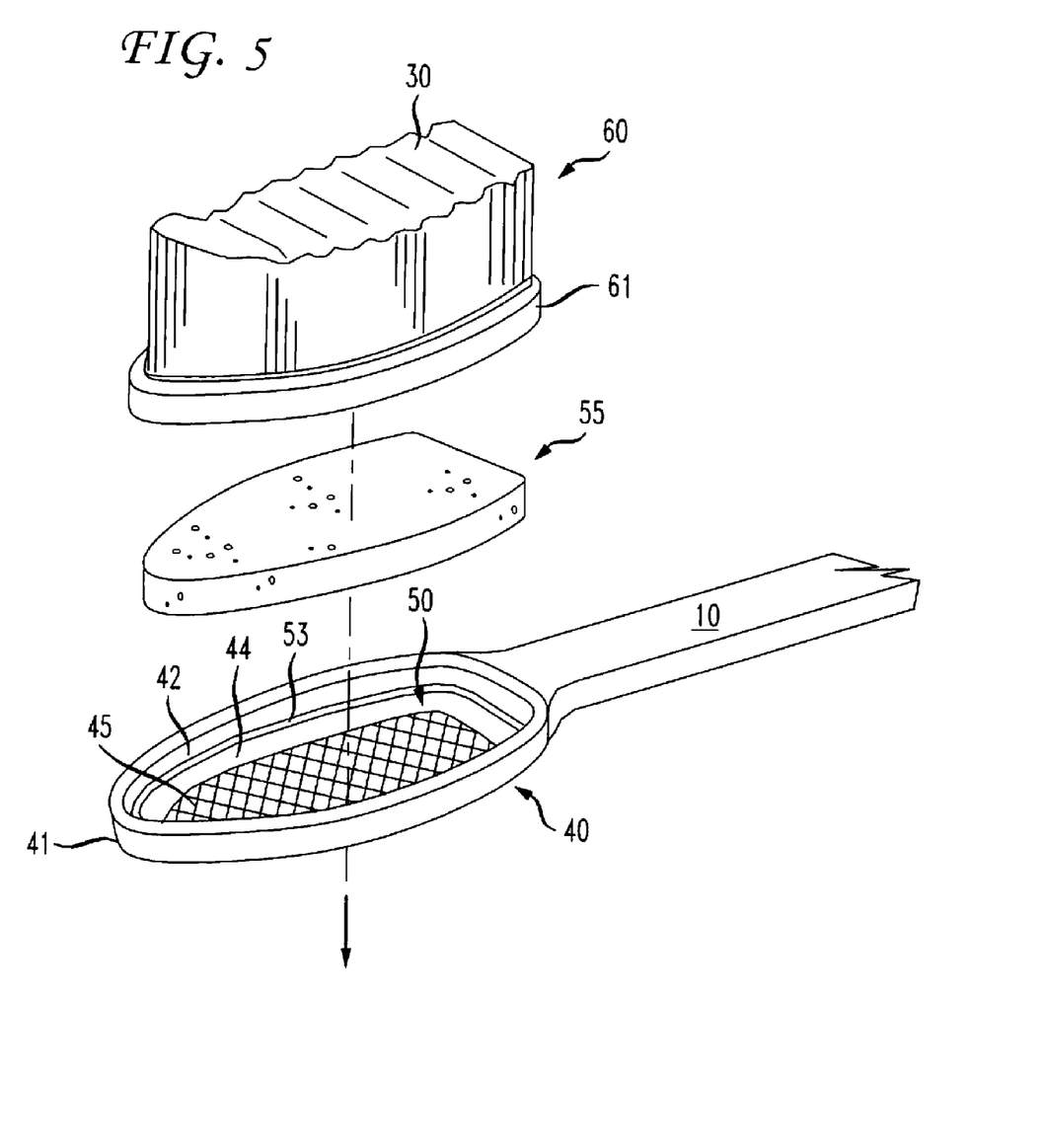
FIG. 5 is a an exploded assembly view of the oral care implement of FIG. 4.

As illustrated in FIGS. 4A, 4B and 5, head 20 of the oral care implement 1 generally includes a base 40 and a tufted insert 60, such as a tufted head plate. When assembled, as shown in FIG. 4A, tufted insert 60 is provided on the base 40 so as to form one or more cavities 50.

Broadly, the oral implement 1 provides head 20 configured to house at least one oral care active agent for introduction into the mouth to perform an intended function. In an embodiment, the oral care agent(s) can be provided in one or more cavities 50 formed in the head 20. The cavities 50 are capable of receiving, retaining, and holding one or more of the dispensable oral care agents. The cavities 50 can receive or hold these agents in liquid or semi-liquid forms, such as structured gel; and solid forms, such as a slow-dissolve wafer, a "hard candy" form, compressed powder; or a mixture of the two such as liquid dispersed in a porous foam. The cavities may also receive a plurality of oral care active agents in a variety of formats. In an embodiment, the cavities 50 will receive and retain the oral care agent(s) until a predetermined amount has been received or the cavity is filled. The composition of the material within the cavities and the size and shape of the cavities themselves can be varied to ensure the best delivery for a variety of beneficial oral care agents. As will be described in more detail later, cavity 50 may house one or more oral care agents to be dispensed during use of the oral care implement 1.

With continued reference to FIGS. 4A, 4B and 5, base 40 includes housing 41 and membrane 45. Housing 41 may be shaped so as to facilitate use in an oral care implement. For illustrative purposes, base 40 may be described as having an outer wall of housing 41, vertical walls 42, 44, 46 and horizontal walls 43, 53. The vertical walls 42, 44, 46 and horizontal walls 43, 53 may be arranged in various configurations depending on the specifics of the shape, design, material of the oral care implement including the elongated handle 10 and/or housing 41. Likewise, base 40 may have greater or fewer numbers of walls 42, 43, 44, 46, and 53 as the description of these walls is not limiting and instructive as to an illustrative structure to aid in assembly and stability of the head. Base 40 of the head 20 can be formed at the same time as handle 10 as a unitary component. Alternatively, the head 20 can be manufactured as a component that is assembled as part of the oral care implement 1. The head 20 components can be attached or joined through a number of techniques including welding via ultrasonic, laser, or through mechanical methods that also permit the head 20 to be removed and discarded.

As shown in FIGS. 4A and 5, membrane 45 has a cavity side 48 and an exterior side 49. In these illustrative figures, the cavity side 48 is the side of the membrane 45 immediately adjacent to cavity 50. Various materials and structural configurations for membranes may be used. For example, in woven or molded arrangements, nylons, plastics or various filament materials may be utilized. The membrane may be formed by filaments, generally configured or laced in any of numerous patterns. Also, the membrane 45 may be a generally flat plastic member with one or more holes or punctures in it so as to allow a substance to flow through the plastic member. The porosity of the membrane 45 can be adjusted to control the flow the amount of material released from the active insert. As depicted in FIG. 4A, one or more substances may flow through the membrane 45 in one or more directions. For example, substances may flow from the cavity side 48 to exterior side 49 and into a user's mouth for application of an oral care agent. Alternatively, the membrane 45 may be configured such that substance such as water or saliva or other activators flow in the reverse direction, from exterior side 49 to cavity side 48. Illustrative flow arrows 145 demonstrate illustrative flow paths as described, While the membrane 45 may be disposed in a generally central region of the surface of the base 40, it can be provided in different parts of the head or portions thereof. Housing 41 surrounds the perimeter edges of the membrane 45 and may provide support and/or stability to the membrane including during use in the mouth. Membrane 45 may be permanently or temporarily affixed to housing 41 by methods including melting, bonding, snap fit and the like. Further, various other configurations are contemplated, as the membrane may be shaped such that it forms a substantial entirety of the second surface 24 of the head 20 of the oral care implement. In such an instance, the membrane may be affixed to the housing 41 by any of a number of mechanisms on its first side 48 or second side 49 in addition to or in lieu of being affixed to housing 41 at its perimeter edges. Also, membrane 45 may be molded in a unitary manner along with handle 10 and head 40.

In the illustrative configuration of FIGS. 4A, 4B and 5, walls 42, 43, 44, 46, and 53 are configured to form ledges and sidewalls respectively for housing each of the membrane 45, the active insert 55 and the base 61 of the tufted insert 60 so that they are fixed together permanently or temporarily. If desired, a securing feature 118 such as a groove or an overhang member may also be utilized to guide and/or secure the base 61 to the base 40 of the head 20. Securing feature 118 may include a physical mechanism alone or in combination with an adhesive substance. Various configurations may be utilized for the securing feature.

Referring to FIGS. 4A, 4B, 5, 6A and 6B, tufted insert 60 is illustratively shown herein as including a base 61 and oral care elements 30 which include teeth cleaning elements 35. Oral care elements 30 can be fixed to the head 20 by a various methods including bonding, molding, melting, and mechanical fixing, including anchor free tufting (AFT) technology. Here, the oral care elements 30 are fixed to the base 61 of the tufted insert 60. The base 61 may also contain conduit 65 that includes one or more orifices, holes, or passageways for permitting any of various substances, including oral care agents to flow bidirectionally between cavity 50 and exterior side 63 of base 61. For example, oral care agents contained in cavity 50 are permitted to travel through base 61 of the tufted insert 60 to the oral care elements 30 on exterior side 63. Likewise, fluids are permitted to flow in the reverse direction from the exterior side 63 through base 61 to cavity 50. An illustrative example of such a fluid may be water or saliva from the mouth of a user that may be utilized as a catalyst or activator for an active material 55 housed in the cavity 50.

Figure 6A:
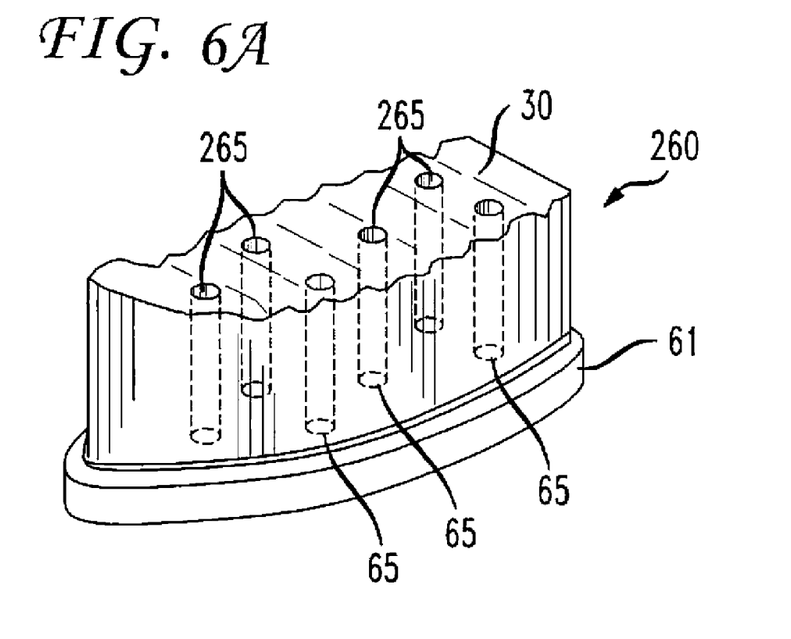
FIGS. 6A and 6B are perspective views of alternative constructions of a tufted insert similar the insert shown in FIG. 5.
Figure 6B:
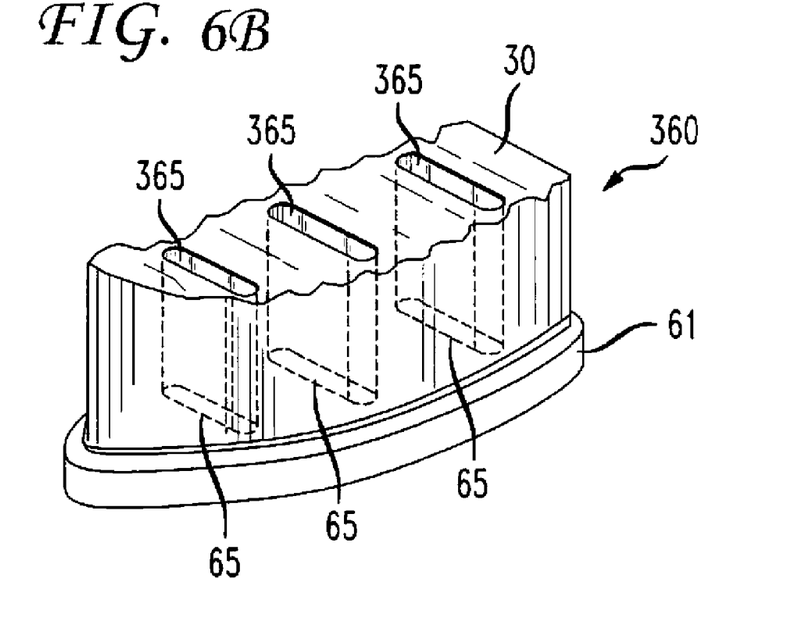

The conduit 65 may include various physical configurations, cross-sectional shapes, and materials depending on flow characteristics including flow rate, particle size, solubility and the like. For illustrative purposes the conduit 65 may include apertures or pipes having circular, polygonal, and irregular cross-sections and/or may also be formed with a mesh, screen, or filtering type structure. Flow arrows 64 illustrate the flow of various substances in both directions through conduit 65 and more generally through base 61 of the tufted insert 60. The conduits configurations regulate, impede, restrict or prohibit flow such that flow occurs in varying degrees in predominately or exclusively in one direction consistent with that described. For example, flow through the base 61 may only be from exterior side 63 to cavity 50 or only in the reverse direction (cavity 50 to exterior side 63), or in both directions as controlled by the membrane 45 or conduits 6D.

Tufted insert 60 is generally shaped and configured in alignment with the shape of base 40 so as to permit these components to be assembled together. FIG. 5 shows an exploded view of an oral care implement 1 and particularly a head 20 having a tufted insert 60, a cavity 50, an active insert 55, and a base 40. To construct the oral care implement, these elements shown in FIG. 5 are assembled as shown in FIG. 4. While the order of assembly may generally vary, active insert 55 is positioned into the cavity 50 usually prior to attachment or connection of the tufted insert 60 and base 40. In various configurations these features may be permanently or temporarily affixed together. For example, the oral implement 1 could be refillable in which the active insert 55 or different active inserts may be removed and reinserted or replaced.

There are a number of forms of the active insert 55, it may be a solid dissolvable tablet or a liquid encapsulated in a dissolvable or breakable outer cover (e.g., a container). The active insert 55 may comprise an oral care material or oral care active agent. Non-limiting examples of active agents which can be used include antibacterial agents, whitening agents, anti-sensitivity agents, anti-inflammatory agents, anti-attachment agents, plaque indicator agents, flavorants, sensates, breath freshening agents, gum health agents and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, minerals, hydrogen peroxide, urea peroxide, sodium percarbonate, PVP-H2O2, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil.

The oral care agent(s) and/or its medium can be selected to complement a toothpaste formula, such as by coordinating flavors, colors, aesthetics, or active ingredients. A flavor can be administered to create a gradual flavor change during brushing, which presently is not possible using toothpaste alone. The flavor changes described here along with other changes in sensation can also be used as a signal for indicating that an effective brushing routine is complete. In one example, the flavorings could be released to indicate that the oral care element 1 is functioning properly or to indicate that the implement 1 is exhausted and ready to be disposed or refilled. A colorant can be added to create a color change during use. Flavor and/or color can also be used to signal another benefit, such as tooth whitening or anti-bacterial action.

The active agent may be compatible with toothpaste, or may be unstable and/or reactive with typical toothpaste ingredients. The active agent also may be a tooth cleaning agent to boost the overall efficacy of brushing.

The active agent can be provided in any suitable vehicle, such as in aqueous solution or in the form of gel or paste. The vehicle can have a variety of different visual aesthetics including clear solution or gel or opaque solution or gel. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the active agent and the desired properties of the medium, such as viscosity. Examples of tooth whitening compositions are described in U.S. Pat. Nos. 6,770,266 and 6,669,930, the disclosures of which are hereby incorporated by reference.

Table I illustrates a cetylpyridinium chloride gel to be dispensed from within the cavity as during brushing as an antibacterial agent.

TABLE I

| Ingredient | Wt % |
| --- | --- |
| Carbopol 974P | 2-5 |
| PEG 600 | 10 |
| FD&C blue #1(1% solution in water) | 0.5 |
| Cetylpyridinium chloride | 20 |
| Water | Q.S. |

Table II example shows the composition of a breath protection solid slow-dissolve wafer to be dispensed from a cavity as described herein.

TABLE II

| Ingredient | Wt % |
| --- | --- |
| Hyroxyethyl cellulose | 20 |
| Hydroxypropylmethyl cellulose | 30 |
| Propylene glycol | 10 |
| Triclosan | 20 |
| Zinc gluconate | 20 |

In one construction, head 20 and/or base 40 may be configured such that active insert 55 may be removed and/or replaced without disassembling head 20. For example, an opening may be positioned on the head such that an existing active insert is removed and a new active insert is placed in the cavity without disassembling the head 20. Further, since a replacement active insert 55 may only need to be placed in the cavity after the previous active insert has been used up, only addition and not removal of an insert may be required. As such, a smaller opening for only insertion of a new active insert 55 may be integrated into the oral care implement design. A slot can be provided on the distal tip of the head sized in accordance with the height of the cavity 50. The slot may be sealable or lockable to prevent opening during brushing. In another construction, the oral care implement may also be configured as a disposable device such that once the active insert 55 is completely used, the device can be discarded.

For further illustrative purposes, FIGS. 6A and 6B illustrate views of exemplary constructions of a tufted insert. Each illustrative tufted insert 260, 360 is shown with conduits 65 and various configurations associated therewith. As described, numerous configurations may be utilized as is understood by those skilled in the art, as FIGS. 6A and 6B are not limiting examples. In FIGS. 6A and 6B, oral care elements 265, 365 (e.g., tooth cleaning elements) extend upwardly from the apertures of the conduits 65. The oral care elements 265, 365 have a hollow interior forming a lumen for fluid communication with the active insert 55 and active agent(s) therein. The oral care elements 265, 365 can be formed of any elastomeric material known for use in tooth cleaning. With this arrangement, dentifrice and/or active agent stays near the tips of the oral care elements 265, 365 during a brushing operation for efficient cleaning and delivery of tissues of the mouth. To provide comfort as well as cleaning benefits, the elastomeric material has a hardness property in the range of A15 to A35 Shore hardness; A20 to A30 Shore hardness; or A25 to A28 Shore hardness. As an example, one elastomeric material is styrene-ethylene/butylene-styrene block copolymer (SEBS) manufactured by GLS Corporation. Nevertheless, SEBS material from other manufacturers or other materials within and outside the noted hardness range could be used. Oral care element 265, 365 can be of desired shape. Oral care element 265 is provided in a cylindrical arrangement. Oral care element 365 can be an elliptical shape or a rectangular with rounded corners in cross-section. Nevertheless, other shapes are possible.

Figure 7:
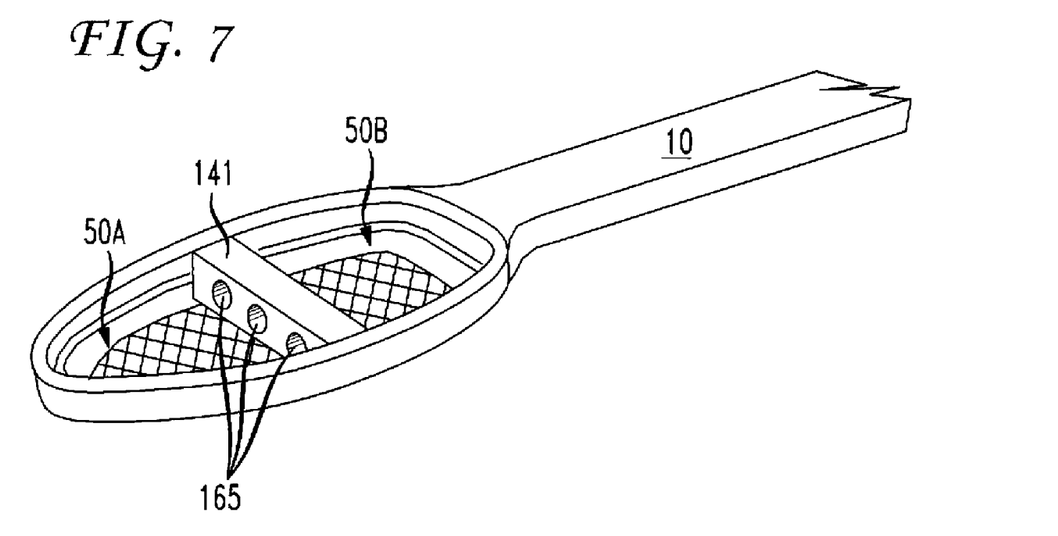
FIG. 7 is a perspective view of an alternative head construction of an oral care implement.
Figure 8:
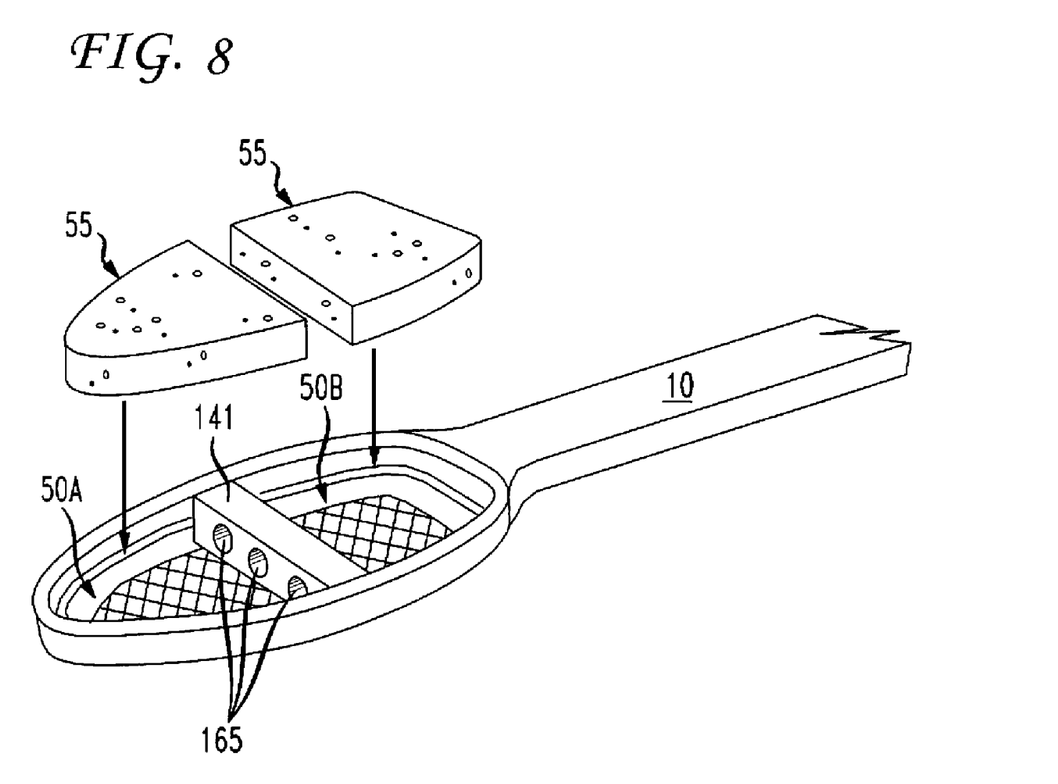
FIG. 8 is a perspective view of the alternative head construction of an oral care implement of FIG. 7 including an active oral care agent.

FIGS. 7-12 show other examples of an oral care implement construction. FIGS. 7 and 8 illustrate a perspective view of the head 20 of an oral care implement including base 40, cavity 50 and tufted insert 60. Here, base 40 further includes separator 141. Separator 141 is depicted as a rectangular member; however, members of various shapes and cross-sections may be utilized. Separator 141 may be formed of the same material as the remainder of base 40 or it may be formed of a different material. Also, separator 141 may be formed as a permanent feature of base 40 such as in a unitary molding or as a detachable or removable component.

Separator 141, as shown in FIGS. 7 and 8, divides cavity 50 into two subcavities 50A and 50B disposed longitudinally in the head 20. In one construction, a transverse separator 141 may include multiple members thereby further dividing the cavity 150 into additional sub-cavities. Separator 141 is currently depicted as having horizontal conduits 165 allowing passage of substance from subcavity 50A to 50B and vice versa. However, the separator may be a solid member or a member without a conduit connecting subcavities 50A and 50B depending on the application. For example, two subcavities can be completely separated. As such, a member without the conduits 165 such as a solid member may be utilized. FIG. 8 illustrates the cavity 50 housing multiple active inserts 55 as described.

Figure 9:
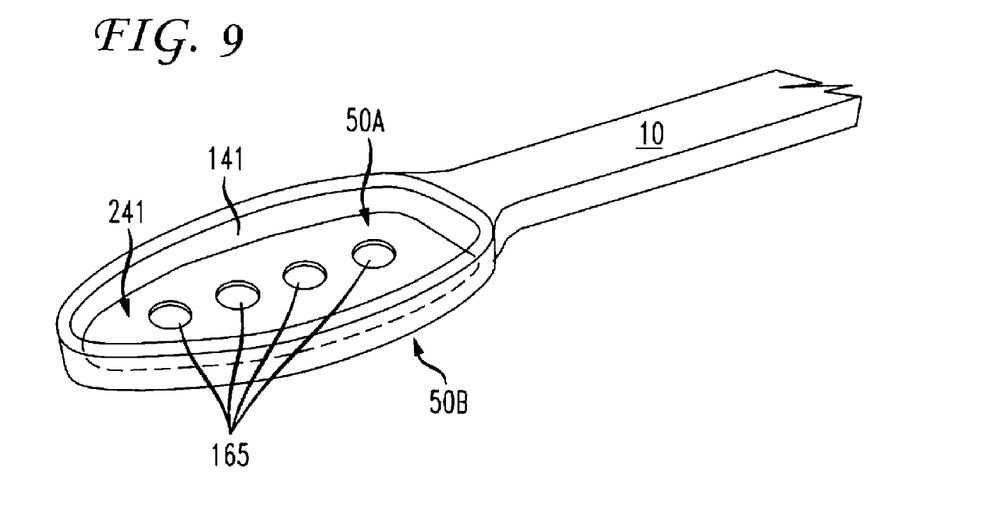
FIG. 9 is a perspective view of an alternative head construction of an oral care implement.
Figure 10:
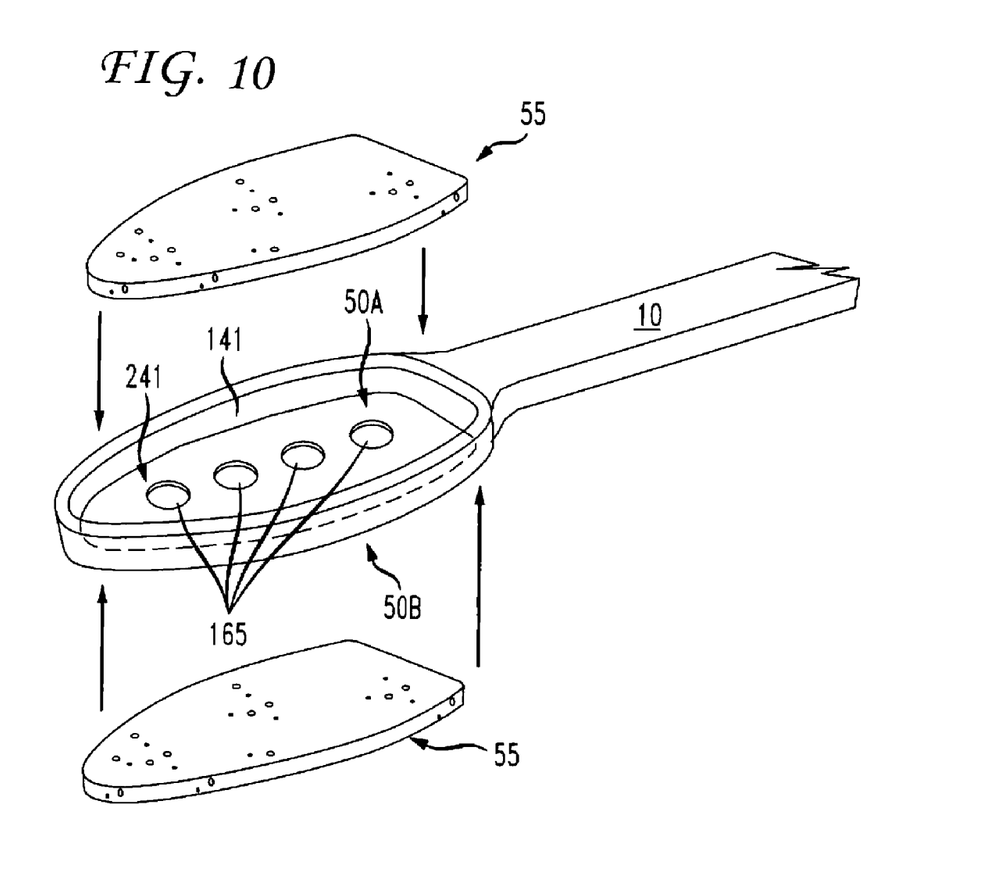
FIG. 10 is a perspective view of the alternative head construction of an oral care implement of FIG. 9 including an active oral care agent.

FIGS. 9 and 10 show other examples of an oral care implement construction. In this construction, separator 141 includes a horizontal sheet member that divides cavity 50 into two subcavities 50C and 50D. Here, the subcavities are arranged vertically in contrast to the illustrative embodiment of FIG. 8 in which the subcavities 50A and 50B align longitudinally.

Figure 11:
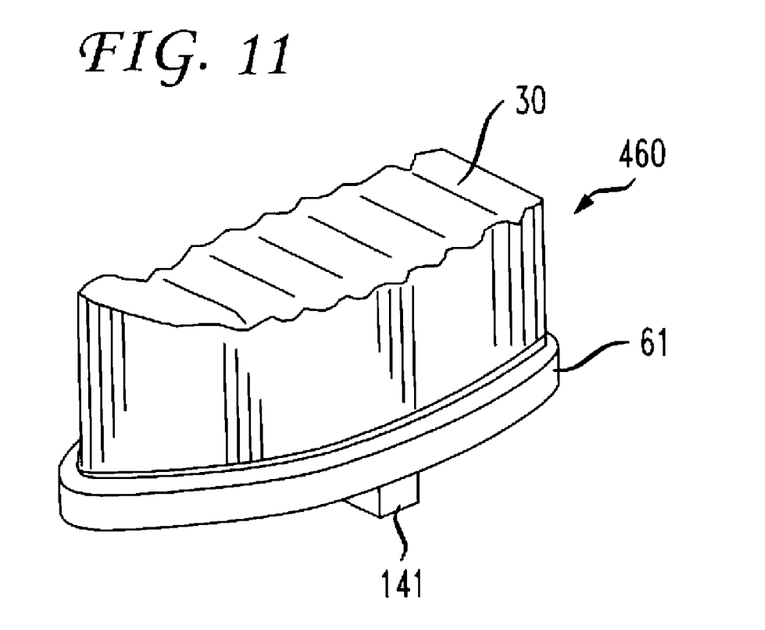
FIG. 11 is a perspective view of an alternative construction of a tufted head plate of an oral care implement.
Figure 12:
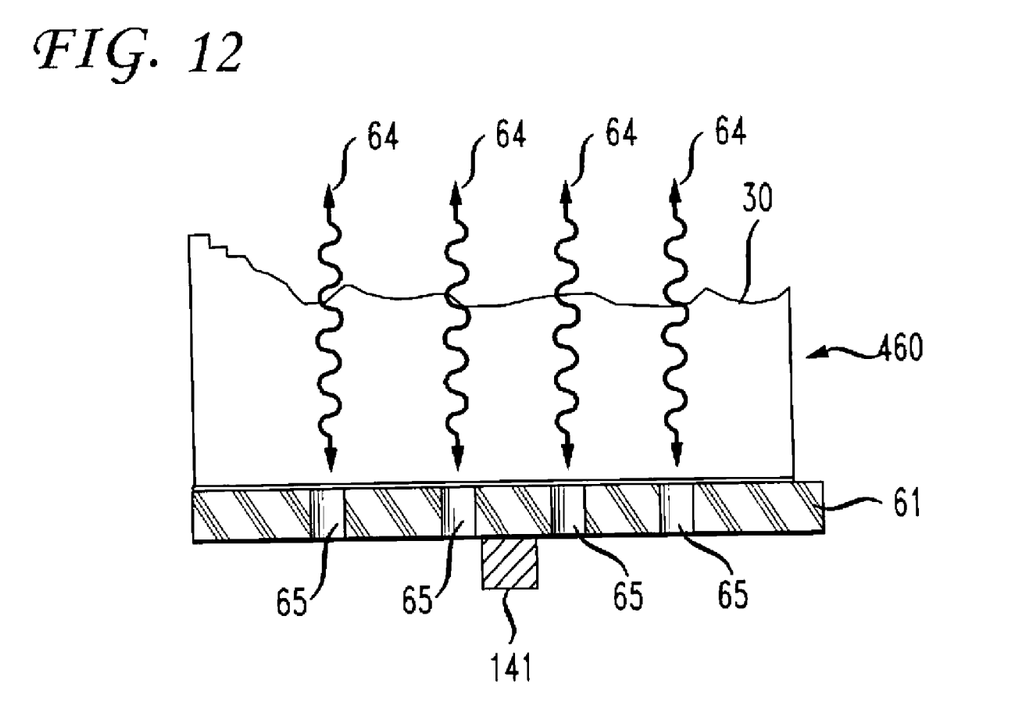
FIG. 12 is a side view of the tufted head plate of an oral care implement of FIG. 11.

FIGS. 11 and 12 show an alternative oral care implement construction. In this construction, a tufted insert 460 further includes a separator 141 attached to or formed as part of the base 61 of the tufted insert. As such, when the head is constructed, the cavity may be divided into a plurality of subcavities as described above with respect to the arrangements of FIGS. 7 and 8. This configuration provides a reusable or refillable variety in which multiple active inserts 55 are retained in the head 20 the oral care implement without changing the head cavity. This configuration provides an alternative manufacturing method of the oral care implement 1 such that only tuft insert has the separator. Hence, multiple oral care implements can be construction with an open cavity without additional manufacturing costs.

A variety of materials may be used to form the head 20 and can include any one of a wide variety of commercially available polymers. In one construction, the oral care implement 1 is molded from a polypropylene, such that upon manufacture it is formed with one or more internal cavities. It is understood that a wide variety of material specifications may be used to provide an oral care implement 1 having various advantageous characteristics including cavity sizing, shape and spacing. For example, the oral care implement 1 can have cavities 50 that deliver oral care agent(s) into the mouth of a user at different rates. These rates can be controlled, for example, by the size of the exposed surface area of the respective cavity 50 and contained oral care agent in the outer surface 22, 24, 26 of the head, the shape of the cavities 50, the depth of the cavities 50 and/or the characteristics of the contained oral care active agent(s).

Adjacent cavities 50 can have different sizes in order to accommodate different amounts of oral care agent(s). As a result, the oral care implement 1 can have different oral care active agent release characteristics that control when and how much of each agent is delivered to the oral cavity. The nature of the material within the cavity can also have an effect on release rate. One advantage of having a two (or more) cavities is that different release rates from different cavities would provide for novel treatment strategies or sensory impressions. For example, if the oral care agent in cavity 50A is released faster than cavity 50B, positive sequential effects could be achieved. If cavity 50A contained a plaque dispersant and cavity 50B contained an anti-bacterial agent, this could be quite beneficial in controlling the overall bacterial infection. Or if cavities 50A & 50B contained different flavors or concentrated sensates, their sequential release could provide a changing flavor to the user. This flavor change could make brushing more enjoyable, or it could signal that the user had brushed long enough.

In one construction, once the cavities 50 receive their intended agent, the head 20 may be advantageously used to dispense or release the oral care active agent within the mouth. The agent can be released from their respective cavities 50 when they come into contact with fluids and/or chemicals within the mouth. In one construction, agents can be impregnated in the active insert material and can be released into the mouth while brushing teeth. During the tooth brushing process water and chemicals will come into contact with the agent(s) within the cavities 50 in the head 20. This will cause a process in which the impregnated oral care agent(s) will be released out from the cavities 50 within the head 20. The use of different oral care active agents in cavities 50 of the same head 20 has the capability of providing a synergistic benefit to the user as well as different treatment regimes for treating oral diseases.

As described above, a wide variety of molding techniques may be used to manufacture the oral care implement 1. Further, a wide variety of material specifications and parameters may be used to provide oral care implements having a variety of desired characteristics. For example, in at least one illustrative example, oral care implement 1 may be constructed for permanent use and disposal after the oral care agent has been used up. In such an instance, the cavity 50 of the oral care implement 1 may be filled with an oral care active agent during initial construction.

While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

What is claimed is:

1. An oral care implement, comprising:
   an elongated handle;
   a head coupled to the handle, the head including a first surface, a second surface opposite the first surface, a base having an upstanding wall defining a cavity, a head plate disposed within the cavity and defining a bounds of the cavity, the head plate secured to the base, and a porous membrane located on the second surface of the head, the porous membrane defining a bounds of the cavity;
   the head plate comprising a plurality of tooth cleaning elements extending from the first surface of the head; and
   an active insert disposed in the cavity for fluid communication with the porous membrane.

2. The oral care implement of claim 1, wherein the porous membrane is formed of a woven material.

3. The oral care implement of claim 1, wherein the active insert comprises an oral care agent provided in a solid, a semi-solid, a liquid, a gel or a dissolvable structure.

4. The oral care implement of claim 3, wherein the active insert includes a plurality of active inserts.

5. The oral care implement of claim 4, wherein the plurality of active inserts includes a different oral care agent.

6. The oral care implement of claim 1, wherein the head plate includes a conduit for fluid communication with the active insert; and the conduit forms a passageway from the cavity to the first surface of the head.

7. The oral care implement of claim 6, wherein the plurality of tooth cleaning elements comprise a cleaning element formed of an elastomeric material extending from the conduit.

8. An oral care implement, comprising:
   a head including a cavity and a porous membrane formed of a woven material defining a bounds of the cavity;
   an active insert disposed in the cavity for fluid communication with the membrane;
   the head including a conduit for fluid communication with the active insert, the conduit disposed opposite the membrane and forming a passageway from the cavity to a first surface of the head;
   a cleaning element formed of an elastomeric material extending from the conduit; and
   wherein the cleaning element has a hollow interior that forms a passageway from the conduit to a tip of the cleaning element.

9. The oral care implement of claim 7, wherein the active insert includes a plurality of inserts having different oral care agents.

10. The oral care implement of claim 1, further comprising a plurality of active inserts being separated by a separator member in the cavity.

11. The oral care implement of claim 10, wherein the plurality of active inserts are longitudinally aligned in the cavity.

12. The oral care implement of claim 10, wherein the plurality of active inserts are vertically aligned in the cavity.

13. The oral care implement of claim 10, wherein the separator member includes a conduit.

14. The oral care implement of claim 1, wherein the plurality of tooth cleaning elements comprise bristle tufts.

15. The oral care implement of claim 14, wherein the head plate comprises a conduit to allow a portion of the active insert to exit the cavity, the conduit forming a passageway from the cavity to the first surface of the head.

16. The oral care implement of claim 15, wherein the head plate is a flat plate.

17. The oral care implement of claim 16, wherein at least one of the plurality of tooth cleaning elements has a hollow interior forming a lumen extending from the conduit for fluid communication with the active insert.

18. The oral care implement of claim 17, wherein the at least one of the plurality of tooth cleaning elements comprises an elastomeric material.

19. The oral care implement of claim 1, wherein the head plate includes a member affixed to a cavity side of the head plate for separating a plurality of active inserts.

20. The oral care implement of claim 1, wherein the active insert is replaceable.

21. The oral care implement of claim 1, wherein the active insert comprises an agent or agents selected from the group consisting of antibacterial agents; anti-inflammatory agents; anti-attachment agents; whitening agents; anti-cavity or enamel repair agents, breath freshening ingredients; tooth sensitivity ingredients; nutritional ingredients; tartar control or anti-stain ingredients; enzymes; sensate ingredients; and flavors or flavor ingredients; and combinations thereof.

22. The oral care implement of claim 1, wherein the active insert comprises an active agent or agents selected from the group consisting of (i) an antibacterial agent selected from the group consisting of chlorhexidine, cetyl pyridinium chloride, triclosan, zinc salts; (ii) a whitening agent selected from the group consisting of hydrogen peroxide, urea peroxide, sodium percarbonate, and PVP-H2O2; (iii) a gum health active selected from the group consisting of polyphenols, triclosan, ethyl pyruvate, and guanidinoethyl disulfide; (iv) a nutritional ingredient selected from the group consisting of vitamins, minerals, and folic acid; (v) a tartar control or anti-stain agent selected from the group consisting of phosphate salts, polyvinylphosphonic acid, and PVM/MA copolymer; (vi) a flavor or flavor ingredient selected from the group consisting of menthol, carvone, anethole, aldehydes, esters, alcohols, and oils of spearmint, peppermint, wintergreen, sassafras, clove, sage, eucalyptus, marjoram, cinnamon, lemon, lime, grapefruit, or orange; (vii) anti-cavity ingredients selected from the group consisting of sodium fluoride, sodium monofluorophosphate, and stannous fluoride; (viii) anti-sensitivity ingredients selected from the group stannous fluoride, and bioactive glass (ix) colorants or other aesthetic agents; and (x) combinations thereof.

23. An oral care implement, comprising:
   an elongated handle;
   a head comprised of a hard plastic and coupled to the handle, the head including a base, a cavity in the base, and a head plate secured to the base of the head, the head plate having a plurality of bristle tufts mounted thereto, the head plate defining a bounds of the cavity, the head plate having at least one aperture forming a passageway from the cavity to a first surface of the head;
   an active insert disposed in the cavity for fluid communication with the aperture; and a porous membrane located on a second surface of the head opposite the first surface, the porous membrane defining a bounds of the cavity, the active insert in fluid communication with the porous membrane.

24. The oral care implement of claim 23, wherein the active insert comprises an oral care agent.

25. The oral care implement of claim 23, wherein the active insert comprises an oral care agent provided in a solid, a semi-solid, a liquid, a gel or a dissolvable structure.

26. The oral care implement of claim 25, wherein the active insert includes a plurality of active inserts.

27. The oral care implement of claim 26, wherein each of the plurality of active inserts includes a different oral care agent.

28. The oral care implement of claim 23, further comprising an elastomeric cleaning element extending from the aperture.

29. The oral care implement of claim 28, wherein the elastomeric cleaning element comprises a hollow interior forming a lumen in fluid communication with the active insert.

30. The oral care implement of claim 23, wherein the active insert comprises an agent or agents selected from the group consisting of antibacterial agents; anti-inflammatory agents; anti-attachment agents; whitening agents; anti-cavity or enamel repair agents, breath freshening ingredients; tooth sensitivity ingredients; nutritional ingredients; tartar control or anti-stain ingredients; enzymes; sensate ingredients; and flavors or flavor ingredients; and combinations thereof.

31. The oral care implement of claim 23, wherein the active insert comprises an active agent or agents selected from the group consisting of (i) an antibacterial agent selected from the group consisting of chlorhexidine, cetyl pyridinium chloride, triclosan, zinc salts; (ii) a whitening agent selected from the group consisting of hydrogen peroxide, urea peroxide, sodium percarbonate, and PVP-H2O2; (iii) a gum health active selected from the group consisting of polyphenols, triclosan, ethyl pyruvate, and guanidinoethyl disulfide; (iv) a nutritional ingredient selected from the group consisting of vitamins, minerals, and folic acid; (v) a tartar control or anti-stain agent selected from the group consisting of phosphate salts, polyvinylphosphonic acid, and PVM/MA copolymer; (vi) a flavor or flavor ingredient selected from the group consisting of menthol, carvone, anethole, aldehydes, esters, alcohols, and oils of spearmint, peppermint, wintergreen, sassafras, clove, sage, eucalyptus, marjoram, cinnamon, lemon, lime, grapefruit, or orange; (vii) anti-cavity ingredients selected from the group consisting of sodium fluoride, sodium monofluorophosphate, and stannous fluoride; (viii) anti-sensitivity ingredients selected from the group stannous fluoride, and bioactive glass (ix) colorants or other aesthetic agents; and (x) combinations thereof.

* * * * *